(12) United States Patent
Posada Escobar et al.

(10) Patent No.: US 7,380,463 B2
(45) Date of Patent: Jun. 3, 2008

(54) ASSEMBLY FOR TESTING PANELS UNDER SHEAR-COMPRESSION LOADS

(75) Inventors: Jesus Posada Escobar, Madrid (ES); Pedro Galvez Lumbreras, Madrid (ES); Angel Manuel Gago Tripero, Madrid (ES)

(73) Assignee: EADS Construcciones Aeronauticas, S.A., Madrid (ES)

( * ) Notice: Subject to any disclaimer, the term of this patent is extended or adjusted under 35 U.S.C. 154(b) by 229 days.

(21) Appl. No.: 11/408,628

(22) Filed: Apr. 21, 2006

(65) Prior Publication Data

US 2007/0193360 A1   Aug. 23, 2007

(30) Foreign Application Priority Data

Feb. 22, 2006   (EP) .................... 06110272

(51) Int. Cl.
*G01N 3/00* (2006.01)
(52) U.S. Cl. .................... 73/788; 73/818
(58) Field of Classification Search ............. 73/788, 73/818
See application file for complete search history.

(56) References Cited

U.S. PATENT DOCUMENTS

| | | | | |
|---|---|---|---|---|
| 4,208,648 | A * | 6/1980 | Naumann | 338/99 |
| 6,055,867 | A * | 5/2000 | Dunne et al. | 73/849 |
| 6,880,409 | B2 * | 4/2005 | Kawabe et al. | 73/856 |
| 6,931,942 | B2 * | 8/2005 | Uhlik et al. | 73/853 |
| 7,089,803 | B1 * | 8/2006 | Scoville et al. | 73/856 |
| 2002/0173921 | A1 * | 11/2002 | Starostovic et al. | 702/36 |
| 2007/0159160 | A1 * | 7/2007 | Yoon et al. | 324/158.1 |

* cited by examiner

*Primary Examiner*—Max Noori
(74) *Attorney, Agent, or Firm*—Ladas and Parry LLP

(57) ABSTRACT

Assembly for testing a panel (11) made of composite material under different combinations of shear-compression loads using an universal tension load machine (16), comprising metallic sheets (12) configured to form, together with the panel (11), a frame of rectangular shape in the same plane than the panel (11), being said metallic sheets (12) able to transmit external loads to the panel (11), two loading parts (19), having translatable lugs (20) to be connected with the universal tension load machine (16), joined at two opposed sides of said frame and a structure (18) to prevent displacements out of the panel (11).

8 Claims, 3 Drawing Sheets

ASSEMBLY FOR TESTING PANELS UNDER SHEAR-COMPRESSION LOADS

FIELD OF THE INVENTION

This invention relates to an assembly for testing panels under combined shear-compression loads using universal tension load machines, and in particular for testing panels of composite material for aircraft surfaces, and to a method for testing panels using said assembly.

BACKGROUND

In modern Aerospace Engineering, the certification of the primary structure of an airplane is done by testing validation at different structure levels. Testing subcomponents like panels allow finding out possible local failures that can be solved before mounting the component. The use of skin panels, specially carbon fiber reinforced panels, leads to their previous testing under several conditions: pure compression, pure shear and combined compression-shear.

In the prior art, there are known the following two methods to apply combined shear-compression actions on panels.

One method uses a box subjected to bending and torsion in which the panel to be tested is introduced. This method, called "four point bending test", applies (see FIGS. 1 and 2) combined shear 2 and compression 3 actions on a panel 1. It use a box 4 subjected to bending and torsion in which the panel 1 to be tested is mounted. The panel 1 is then subjected to combined shear-torsion loads by means of hydraulic jacks 5.

The main problem of this method is the high cost and the long duration of the whole process, being necessary the manufacturing of a new box for each new test or panel. Besides, in most of the cases, one new box 4 is required for each tested panel 1, because it is very difficult to prevent the damage of said box 4 when the failure of the panel 1 occurs.

Another method uses a special machine to test panels, in which each action (see FIG. 3) compression 7 and shear 8, is applied separately on each tested panel 1 by means of hydraulic actuators 6.

The main disadvantage of this method is that very expensive machines with complex hydraulic and test control systems are necessary. Moreover, these machines are only valid for this kind of tests.

The present invention provides an assembly for testing panels, and in particular skin panels for aircraft surfaces, under combined shear-compression loads, and a method for testing panels using said assembly, that comes to solve previous limitations in the known art.

SUMMARY OF THE INVENTION

The present invention provides an assembly for testing a panel made of composite material, under combined shear-compression loads, using an universal tension load machine that comprises:
  Metallic sheets configured to form, together with the panel, a frame of rectangular shape in the same plane than the panel, being said metallic sheets able to transmit external loads to the panel.
  Two loading parts, having lugs to be connected with the universal tension load machine, joined at two opposed sides of said rectangular frame, said lugs being translatable along said parts in the transversal direction with respect to the frame.
  A structure to prevent displacements out of the panel plane.

The present invention also provides a method of testing a panel using the above-mentioned assembly including the following steps:
  Placing the assembly in an universal tension load machine.
  Applying loads to the assembly through the lugs of the loading parts, being said lugs placed in each loading part so that the desired combination of shear-compression load is obtained.

One advantage of the present invention regarding the prior art is that the required tooling is simple and most of it can be reused for other combined tests.

Another advantage is that only an standard tension load machine is required which can be also used in typical tension-compression tests.

Another advantage is that the total cost and duration of the whole process (design-manufacturing-test) is reduced.

BRIEF DESCRIPTION OF DRAWINGS

The features, objects and advantages of the invention will become apparent by reading this description in conjunction with the accompanying drawings, in which.

DETAILED DESCRIPTION OF PREFERRED EMBODIMENTS

Figure 1:
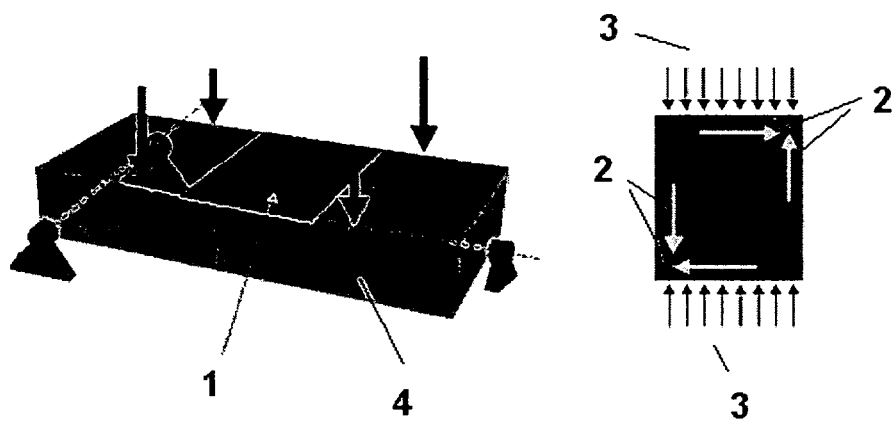
FIG. 1 is a schematic view of the "four point bending test" of the prior art.
Figure 2:
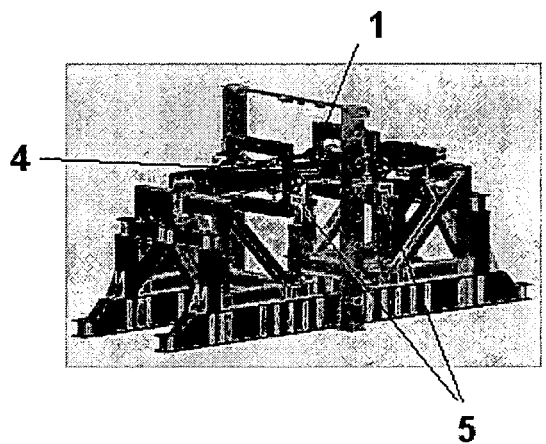
FIG. 2 is a perspective view of the machine used in the "four point bending test" of the prior art.
Figure 3:
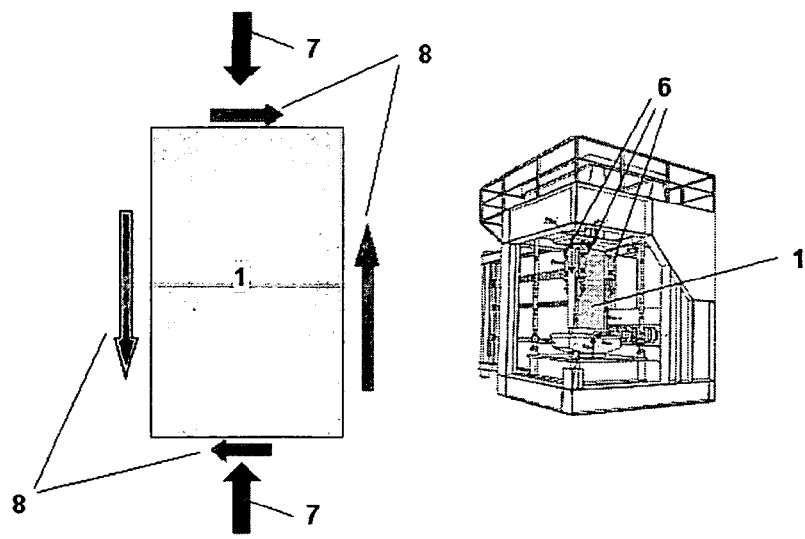
FIG. 3 is a schematic view of the hydraulic actuator machine of the prior art.

The assembly according to the present invention is composed by the following elements: the panel 11, the metallic sheets 12 to transmit the loads to the panel 11, the loading parts 19 with lugs 20 to be connected to the universal tension load machine 16 to apply a load to the assembly, and a structure 18 that prevents displacements out of the test panel 11 plane.

The testing of panel 11 is performed placing the assembly in the universal tension load machine 16 and applying a load to the assembly through the lugs 20 of the loading parts 10.

Figure 4:
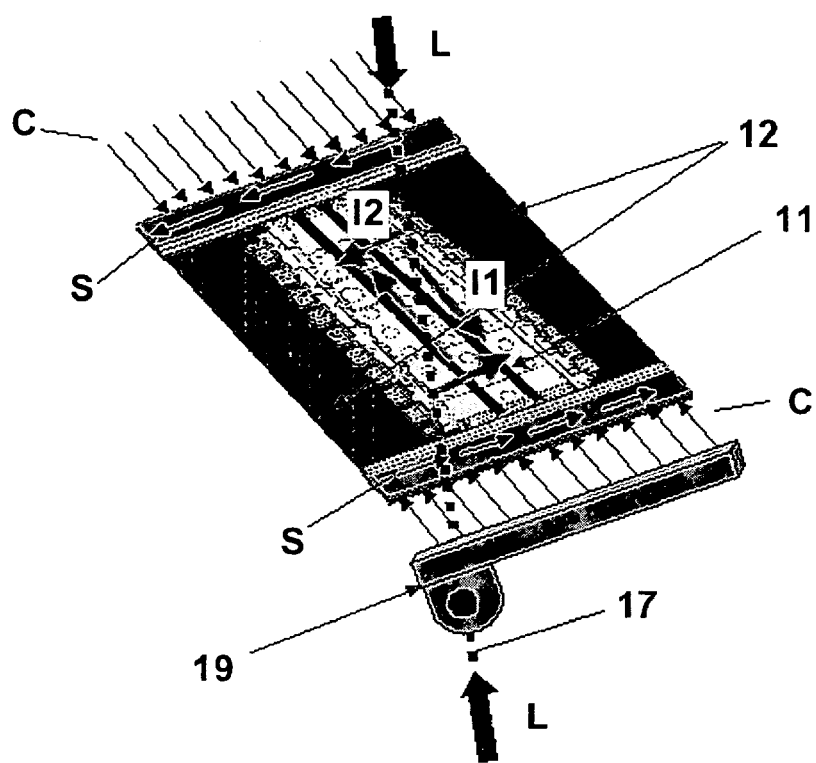
FIGS. 4 shows the main components of the assembly according to the present invention.
Figure 5:
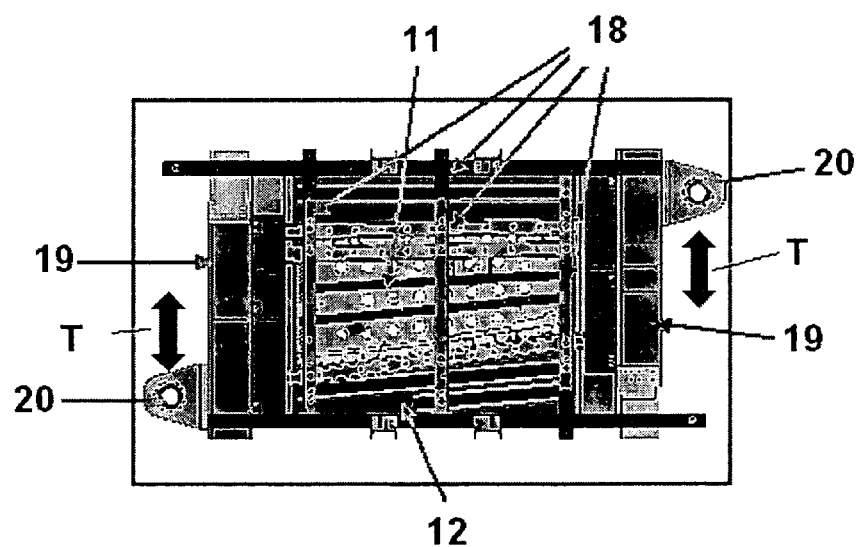
FIG. 5 is a top view of an assembly according to the present invention.
Figure 6:
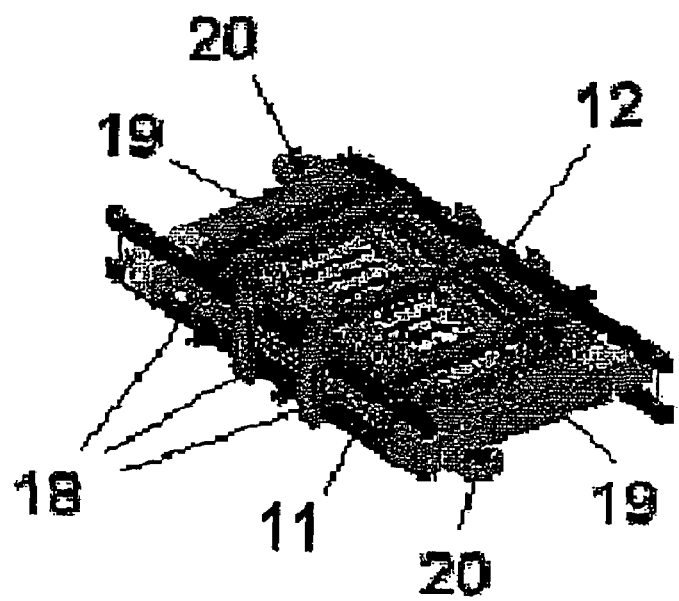
FIG. 6 is a perspective view of an assembly according to the present invention.
Figure 7:
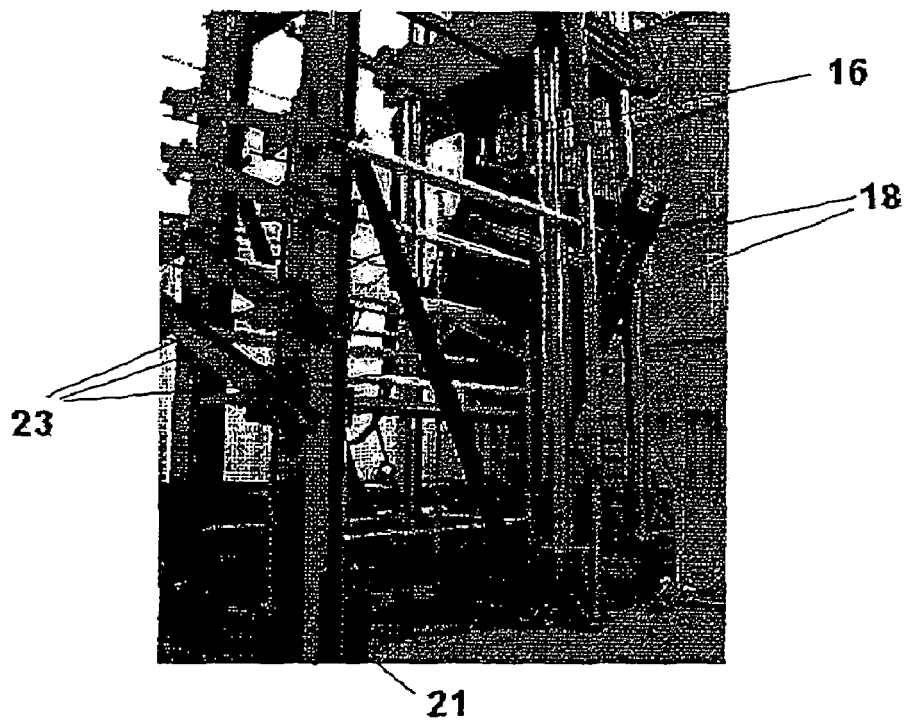
FIG. 7 a perspective view of an assembly according to this invention placed in an universal tension load machine.

As shown in FIG. 4 the load L applied by the universal tension load machine along axis 17 produce shear actions S and compression actions C on the metallic sheets 12 that are transmitted to the panel 11 causing internal actions indicated by arrows 11, 12.

Lugs 20 of the loading parts 19 have the possibility of displacement in transversal direction T in order to obtain different combinations of shear-compression loads on panel 11.

Said structure 18 is preferably a self-supported structure by the own assembly but that can also have long rods 23 for its fixation to an external pillar 21.

Loading parts 19 are reusable for different tests but metallic sheets 12 have to be designed to fit for each specific test. In this respect, the finite elements models show that, due to compatibility of deformations of metallic sheets 12 and test panel 11, with an appropriate selection of the metallic sheets 12 thickness, an appropriate shear-compression status can be achieved in the test panel 11.

Although the present invention has been fully described in connection with preferred embodiments, it is evident that modifications may be introduced within the scope thereof, not considering this as limited by these embodiments, but by the contents of the following claims.

The invention claimed is:

1. Assembly for testing a panel (11), made of composite material, under combined shear-compression loads, using an universal tension load machine (16), characterized by comprising:
   a) metallic sheets (12) configured to form, together with the panel (11), a frame of rectangular shape in the same plane than the panel (11), being said metallic sheets (12) able to transmit external loads to the panel (11);
   b) two loading parts (19), having lugs (20) to be connected with the universal tension load machine (16), joined at two opposed sides of said frame, said lugs (20) being translatable along said loading parts (19) in the transversal direction (T) with respect to the panel (11); and
   c) a structure (18) to prevent displacements out of the panel (11) plane.

2. Assembly according to claim 1, wherein said metallic sheets (12) are made of aluminium.

3. Assembly according to claim 1, wherein said structure (18) to prevent displacements is a structure supported by the own assembly.

4. Assembly according to claim 1, wherein said structure to prevent displacements includes rods (23) for supporting the structure (18) in external pillars (21).

5. Method of testing a panel using the assembly of claim 1, characterized in that includes the following steps:
   a) placing the assembly in an universal tension load machine (16);
   b) applying loads to the assembly through the lugs (20) of the loading parts (19), being said lugs (20) placed in loading part (19) so that the desired combination of shear-compression load is obtained.

6. Method of testing a panel using the assembly of claim 2, characterized in that includes the following steps:
   a) placing the assembly in an universal tension load machine (16);
   b) applying loads to the assembly through the lugs (20) of the loading parts (19), being said lugs (20) placed in loading part (19) so that the desired combination of shear-compression load is obtained.

7. Method of testing a panel using the assembly of claim 3, characterized in that includes the following steps:
   a) placing the assembly in an universal tension load machine (16);
   b) applying loads to the assembly through the lugs (20) of the loading parts (19), being said lugs (20) placed in loading part (19) so that the desired combination of shear-compression load is obtained.

8. Method of testing a panel using the assembly of claim 4, characterized in that includes the following steps:
   a) placing the assembly in an universal tension load machine (16);
   b) applying loads to the assembly through the lugs (20) of the loading parts (19), being said lugs (20) placed in loading part (19) so that the desired combination of shear-compression load is obtained.

* * * * *